United States Patent [19]
Grimard

[11] Patent Number: 5,489,266
[45] Date of Patent: Feb. 6, 1996

[54] SYRINGE ASSEMBLY AND METHOD FOR LYOPHILIZING AND RECONSTITUTING INJECTABLE MEDICATION

[75] Inventor: Jean P. Grimard, Vif, France

[73] Assignee: Becton, Dickinson and Company, Franklin Lakes, N.J.

[21] Appl. No.: 187,232

[22] Filed: Jan. 25, 1994

[51] Int. Cl.$^6$ .......................... A61M 37/00; A61M 31/00
[52] U.S. Cl. .................... 604/89; 604/82; 604/51; 604/191; 604/218
[58] Field of Search .......................... 604/89, 90, 91, 604/187, 218, 221, 82, 191

[56] References Cited

U.S. PATENT DOCUMENTS

| | | |
|---|---|---|
| 2,490,553 | 12/1949 | Smith . |
| 3,164,303 | 1/1965 | Trautmann . |
| 3,680,558 | 8/1972 | Kapelowitz . |
| 3,739,947 | 6/1973 | Baumann et al. . |
| 3,835,855 | 9/1974 | Barr, Jr. . |
| 4,060,082 | 11/1977 | Lindberg et al. . |
| 4,116,240 | 9/1978 | Guiney . |
| 4,465,476 | 8/1984 | Gahwiler . |
| 4,563,174 | 1/1986 | Dupont et al. . |
| 4,599,082 | 7/1986 | Grimard . |
| 4,613,326 | 9/1986 | Szwarc . |
| 4,755,169 | 7/1988 | Sarnoff et al. . |
| 4,952,208 | 8/1990 | Lix . |
| 5,125,892 | 6/1992 | Drudik . |
| 5,364,369 | 11/1994 | Reynolds . |

*Primary Examiner*—C. Fred Rosenbaum
*Assistant Examiner*—Perry E. Van Over
*Attorney, Agent, or Firm*—John L. Voellmicke; Vincent A. Castiglione

[57] ABSTRACT

A syringe assembly includes a substantially cylindrical syringe barrel and a plunger assembly. The plunger assembly includes a distally disposed flow channelizer and a proximally disposed stopper releasably engaged with one another. The stopper includes an aperture engageable with the distal end of a plunger rod. The flow channelizer includes flutes for accommodating an outflow of vapor during lyophilization and to enable efficient mixing of a lyophilized medication and a diluent. Liquid medication in the syringe chamber is lyophilized and a vacuum is applied to the syringe barrel. The plunger assembly then is urged distally into sealing engagement with the syringe barrel. A plunger rod is engaged with the stopper, and is moved proximally to simultaneously separate the stopper from the flow channelizer and to draw diluent into the chamber for reconstituting the previously lyophilized medication.

24 Claims, 6 Drawing Sheets

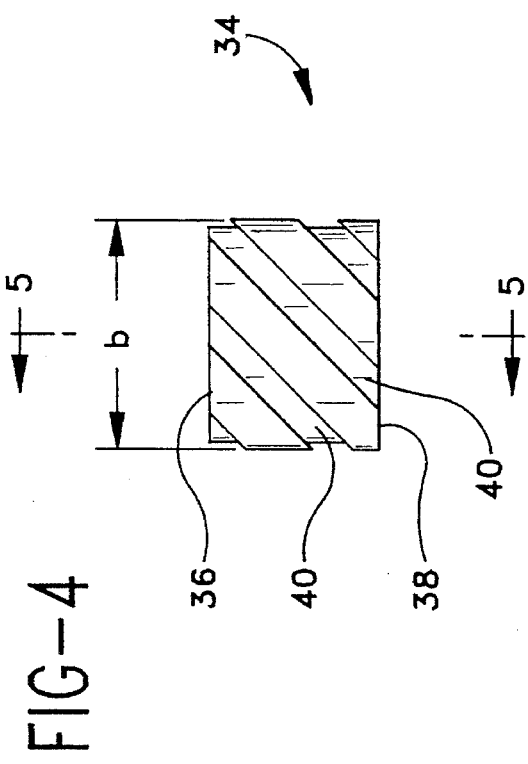
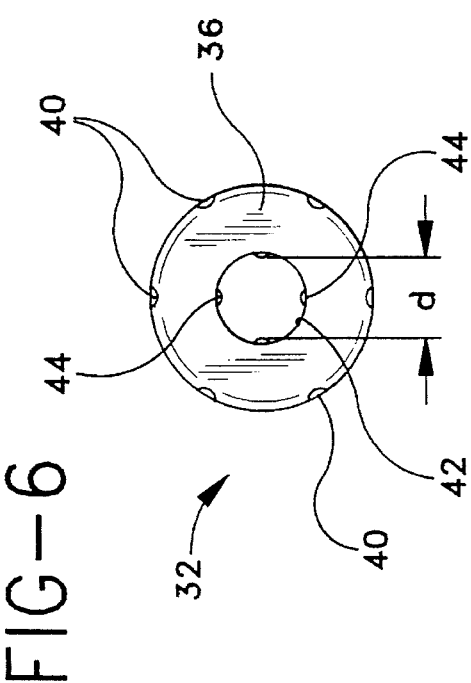
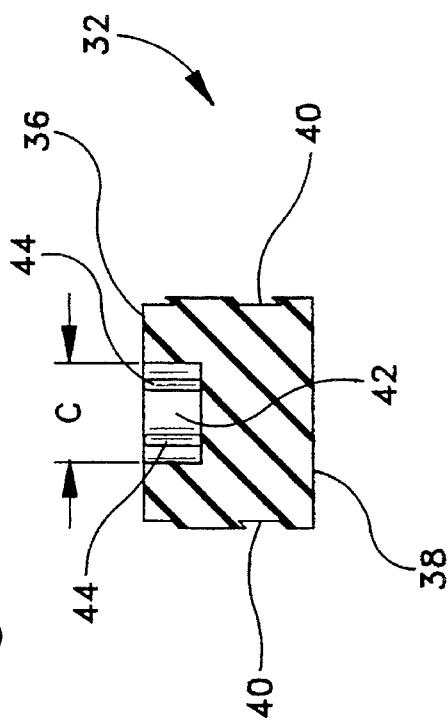

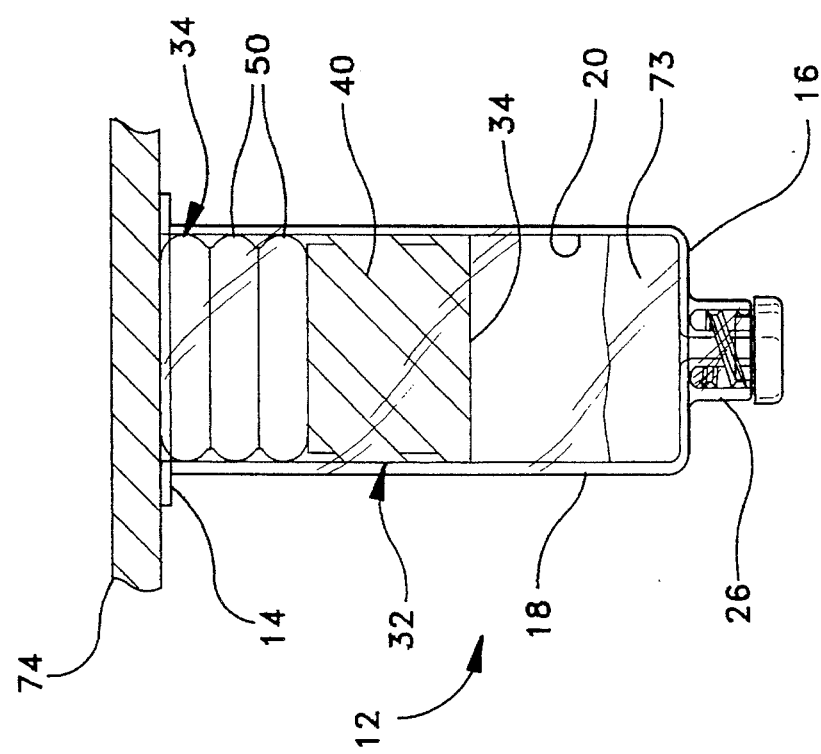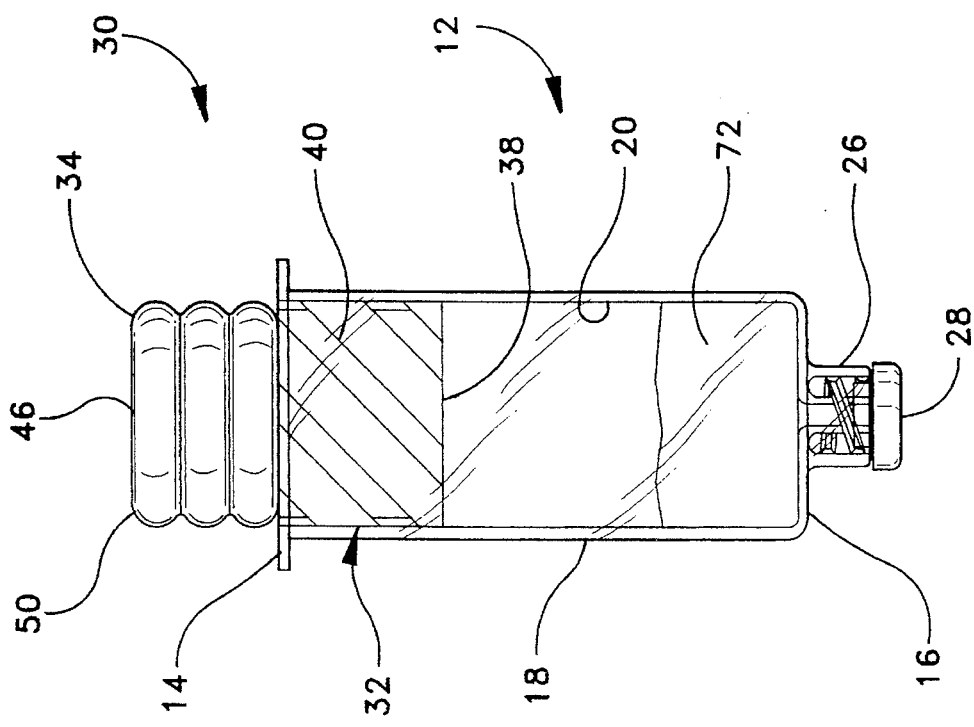

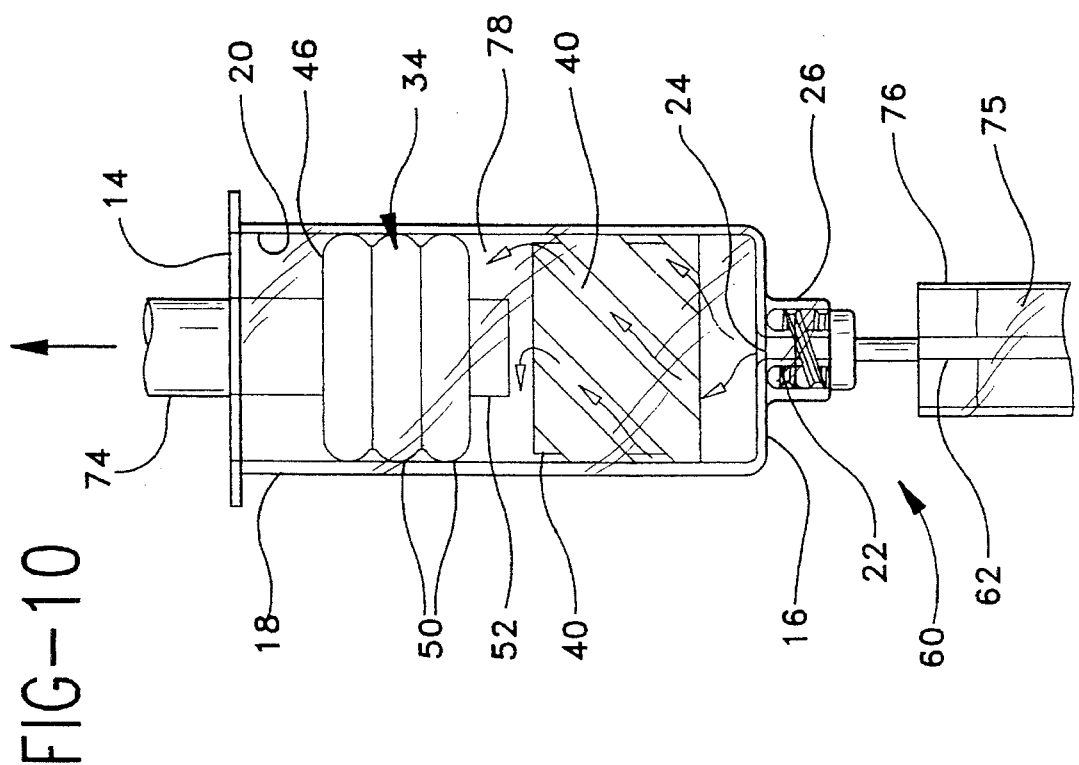
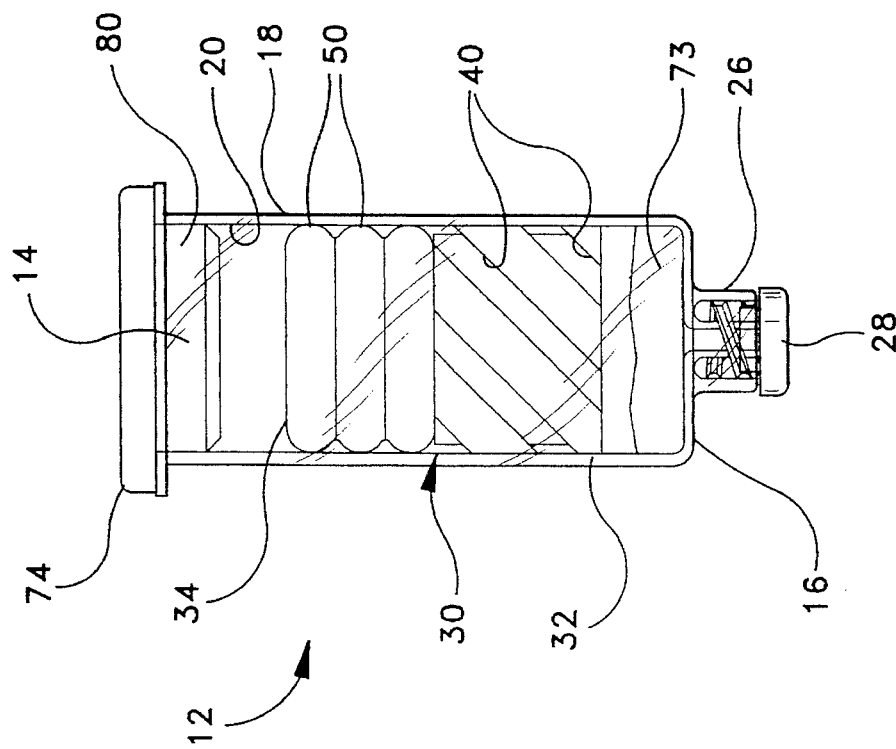

SYRINGE ASSEMBLY AND METHOD FOR LYOPHILIZING AND RECONSTITUTING INJECTABLE MEDICATION

FIELD OF THE INVENTION

The subject invention relates to a hypodermic syringe, a plunger assembly and a process for efficiently lyophilizing an injectable medication and for subsequently reconstituting the lyophilized medication.

DESCRIPTION OF THE PRIOR ART

Liquid pre-filled hypodermic syringes offer many efficiencies. However, many injectable medications degrade rapidly and lose their effectiveness. Refrigeration and special packaging can increase shelf life, but add to cost, complicate storage and offset many efficiencies provided by pre-filled syringes.

Shelf life can be substantially increased by lyophilizing or freeze drying the injectable medication. The lyophilizing process reduces the liquid medication to a dried powdery or granular form. Lyophilized medication can be stored in the chamber of a hypodermic syringe. Shortly prior to use, the lyophilized medication is mixed with a diluent, and the reconstituted medication can be injected from the same hypodermic syringe in which the lyophilized medication had been stored.

The prior art includes hypodermic syringes and vials made of glass or plastic having a chamber with a stopper slidably disposed at an intermediate position. In some prior art syringes, regions of the chamber disposed distally of the stopper are of non-cylindrical shape and define a bypass. A lyophilized medication is stored in the chamber distally of the stopper, while a selected diluent is stored in the chamber proximally of the stopper. A plunger is slidably disposed in fluid-tight engagement with the chamber wall proximally of the diluent. Movement of the plunger in a distal direction urges both the diluent and the stopper toward the lyophilized medication. The stopper eventually will align with the bypass region of the prior art syringe barrel, and further movement of the plunger will cause the diluent to flow through the bypass and into the distal portion of the chamber for mixing with the lyophilized medication. The stopper can be configured to promote a flow pattern of the diluent that will enhance mixing of the diluent with the lyophilized medication. An example of such a hypodermic syringe is shown in U.S. Pat. No. 4,599,082.

The two-component hypodermic syringe assembly described above functions very well. However, it is desired to make improvements. For example, the need for two axial spaced chamber sections along the body of the hypodermic syringe necessitates a longer syringe. The lyophilizing process generally is carried out in the syringe. Thus, the lyophilizing apparatus must be large enough to accommodate the larger syringe. Larger hypodermic syringes and correspondingly larger lyophilizing apparatus are more costly and require more space. Additionally, the need for a non-cylindrical cross-section in the bypass region of the prior art syringe increases costs.

SUMMARY OF THE INVENTION

A lyophilizing syringe assembly in accordance with the subject invention includes a generally cylindrical syringe barrel having an open proximal end, a distal end and a fluid receiving chamber therebetween. The distal end of the syringe barrel defines a tip having a passage extending therethrough and communicating with the chamber. A tip cap is releasably engageable with the tip to seal the passage therethrough. The tip also is configured to releasably receive a needle cannula.

The syringe assembly further includes a two-part plunger assembly. The plunger assembly includes a distally disposed flow channelizer and a proximally disposed stopper releasably engaged with the flow channelizer.

The flow channelizer may be a generally cylindrical member having opposed proximal and distal ends and dimensioned for slidable movement in the chamber of the syringe barrel. The flow channelizer is configured to define one or more fluid flow channels extending from the proximal end to the distal end thereof. The fluid flow channels may define flutes extending along outer circumferential regions. The flutes extend axially and preferably extend in generally helical directions to achieve a swirling mixing of a lyophilized medication and a diluent, as explained further herein. The proximal end of the flow channelizer is configured for releasably receiving distal portions of the stopper.

The stopper of the plunger assembly also is a generally cylindrical structure with opposed proximal and distal ends. The distal end of the stopper may define a mating means dimensioned and configured for engagement with the proximal end of the flow channelizer. The proximal end of the stopper is configured for engagement with a plunger rod. Portions of the stopper between the proximal and distal ends are dimensioned and configured for sliding fluid-tight engagement with the cylindrical chamber wall of the syringe barrel.

The syringe assembly of the subject invention further includes a plunger rod having opposed proximal and distal ends. The distal end of the plunger rod is configured for secure engagement with the stopper of the plunger assembly.

The syringe assembly is used by attaching the tip cap over the tip of the syringe barrel and depositing a dose of liquid medication in the chamber. The flow channelizer and the stopper of the plunger assembly are releasably engaged with one another, and the flow channelizer is slidably inserted into the open proximal end of the syringe barrel. In this partly stoppered condition, the fluid flow channels provide communication between the chamber and regions external of the syringe barrel. The syringe barrel is then subjected to a lyophilization process for freeze drying the liquid medication in the barrel. Liquid portions of the medication in the chamber are frozen solid and then subject to subatmospheric pressure and then, as a gas or vapor, drawn from the syringe barrel through the fluid flow channels in the flow channelizer of the plunger assembly.

Upon completion of the lyophilizing process, a vacuum is applied in the lyophilizing apparatus to reduce pressure in the chamber. The stopper then is urged into sealing engagement with the cylindrical walls of the syringe barrel. The process continues by permitting regions surrounding the syringe assembly to return to atmospheric pressure. This higher pressure will cause the entire plunger assembly to move distally in the syringe barrel and toward the lyophilized medication at the distal end of the chamber.

The syringe barrel with the lyophilized medication therein can be packaged and shipped in the standard manner. The lyophilized medication will be safely protected between the tip cap that is sealingly engaged over the tip of the syringe barrel and the stopper that is sealingly engaged within the chamber of the syringe barrel.

The syringe assembly and lyophilized medication can be used by engaging a plunger rod with the engagement means at the proximal end of the stopper. The tip cap then can be removed from the tip of the syringe barrel and a needle cannula can be mounted thereto. The distal tip of the needle cannula then can be inserted into a diluent, and a proximally directed force can be exerted on the plunger rod. The flow channelizer will be frictionally retained by the cylindrical chamber wall of the syringe barrel. However, the force on the plunger rod will cause the stopper to move proximally in the chamber and to separate from the flow channelizer. This will effectively create a second chamber between the flow channelizer and the stopper. The low pressure created by the formation of this second chamber will draw diluent through the lumen of the needle cannula and into the chamber. The diluent will flow through the lyophilized medication, and the reconstituted mixture will continue through the fluid flow channels of the flow channelizer and into the chamber defined between the flow channelizer and the stopper. The helical configuration of the fluid flow channels in the preferred embodiment creates a vortex mixing for efficient and complete reconstitution of the lyophilized medication. The medication then can be injected in substantially the conventional manner by using the plunger rod in a distal direction.

The syringe assembly of the subject invention does not require a bypass in the syringe barrel, and hence can use the less expensive conventional cylindrical syringe barrel. Additionally, by using a diluent from a separate vial or ampule, a separate space for a diluent is not required in the syringe barrel. Thus, the syringe barrel can be substantially shorter than prior art two-component syringe assemblies, and a smaller lyophilizing apparatus also can be used. The subject syringe assembly also requires only one plunger stopper. Hence, further reductions in the size of the syringe barrel can be achieved, along with corresponding cost savings due to the use of a single plunger stopper and a smaller syringe barrel.

BRIEF DESCRIPTION OF THE DRAWINGS

FIG. 4 is a side elevational view of the flow channelizer.

FIG. 5 is a cross sectional view taken along line 5—5 in FIG. 4.

FIG. 6 is an end elevational view of the flow channelizer of FIG. 4.

FIG. 7 is a side elevational view of the syringe assembly in a first operational condition.

FIG. 8 is a side elevational view similar to FIG. 7, but showing the syringe assembly after lyophilizing and stoppering.

FIG. 9 is a side elevational view similar to FIGS. 7 and 8, but showing the syringe assembly after return to atmospheric pressure.

FIG. 10 is a side elevational view similar to FIGS. 7–9, but showing the syringe assembly during reconstitution of the lyophilized medication.

DETAILED DESCRIPTION OF THE PREFERRED EMBODIMENT

Figure 1:
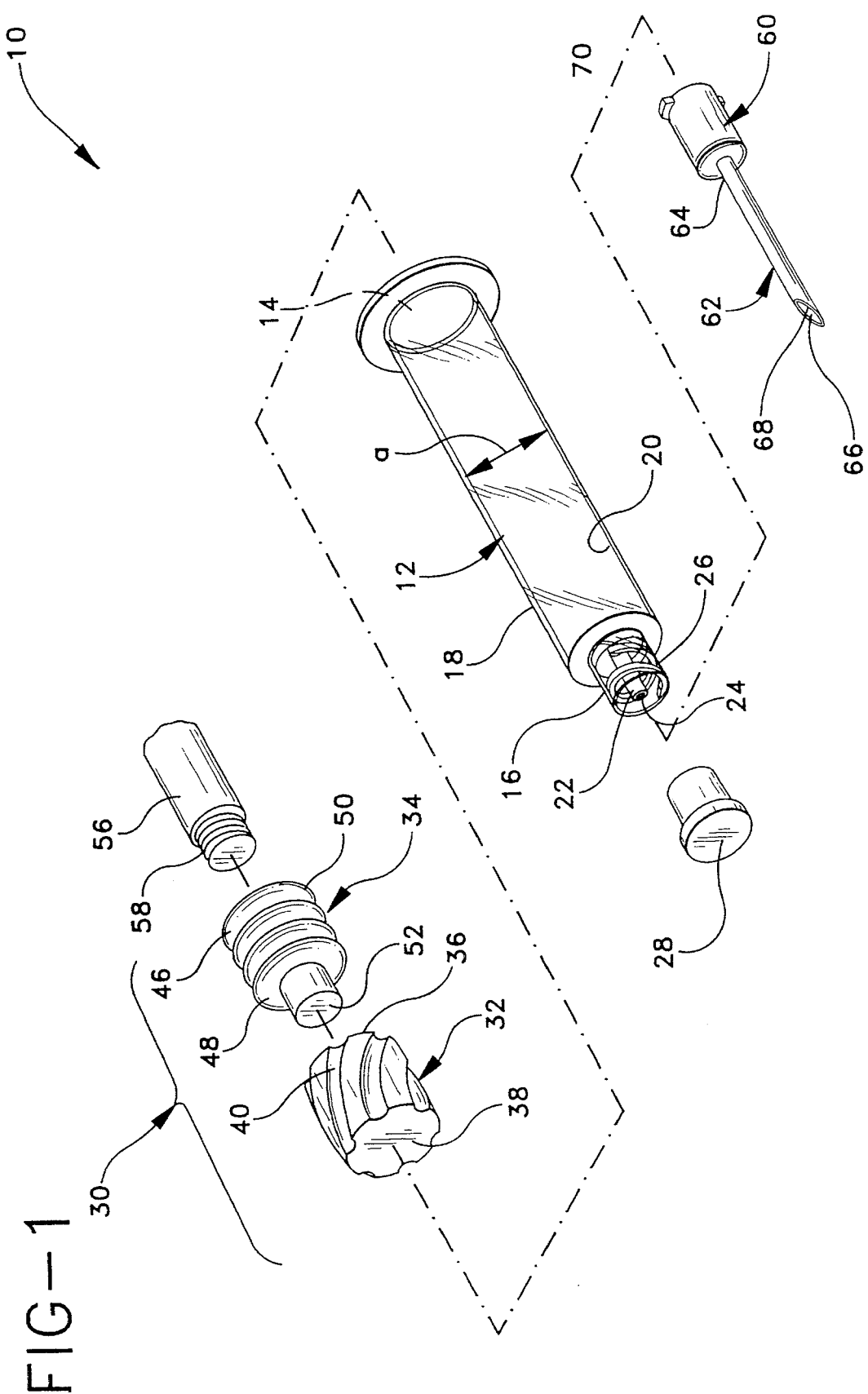
FIG. 1 is an exploded perspective view of a syringe assembly in accordance with the subject invention.
Figure 3:
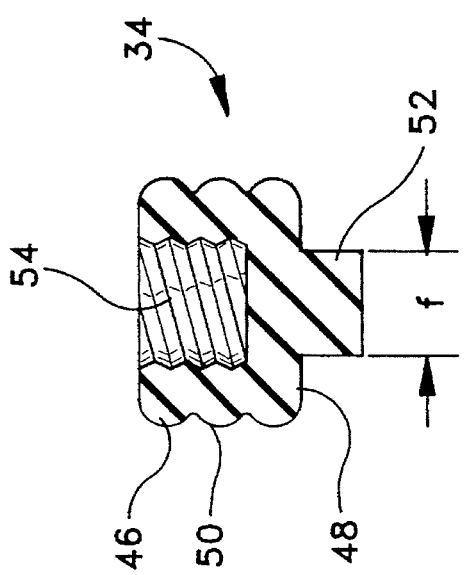
FIG. 3 is a cross-sectional view taken along line 3—3 in FIG. 2.
Figure 2:
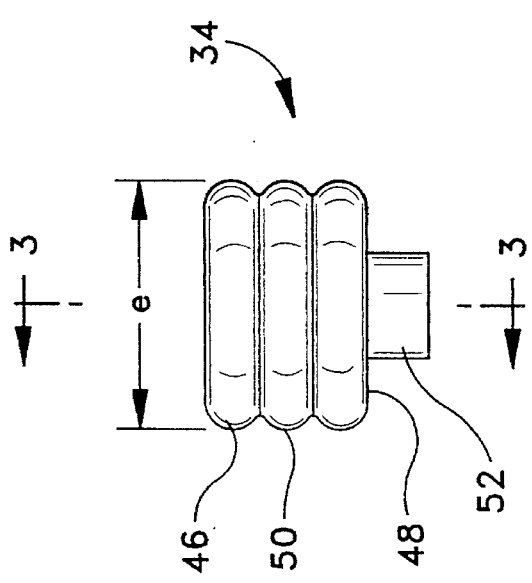
FIG. 2 is a side elevational view of the stopper.

A syringe assembly in accordance with the subject invention is identified generally by the numeral 10 in FIG. 1. Syringe assembly 10 includes a syringe barrel 12 having an open proximal end 14, a distal end 16 and a substantially cylindrical chamber wall 18 extending therebetween. The cylindrical wall has a uniform circularly shaped cross-section without any deformation in the side wall which will allow liquid to flow around stoppers in the barrel. Chamber wall 18 defines a substantially cylindrical fluid receiving chamber 20 of inside diameter "a". Distal end 16 of syringe barrel 12 includes an elongate tip 22 having a passage 24 extending axially therethrough and communicating with chamber 20. A locking luer type collar 26 is disposed substantially concentrically around tip 22, and includes an array of internal threads for threadedly engaging a needle cannula as explained further herein. Although a locking luer type collar is desirable for enhancing the connection between the needle and the syringe, syringe barrels without locking collars are frequently used. Syringe barrels without collars rely in frictional engagement between the barrel tip and the inside of the needle hub to hold the needle on the barrel.

Syringe assembly 10 further includes a tip cap 28 formed from an elastomeric or plastic material and dimensioned for sealingly engaging tip 22 of syringe barrel 12.

The syringe assembly further includes a generally cylindrical plunger assembly 30 as shown in FIGS. 1–6. Plunger assembly 30 includes a distally disposed flow channelizer 32 and a proximally disposed stopper 34 releasably engageable with one another.

Flow channelizer element 32 is made of material such as natural rubber, synthetic rubber or thermoplastic elastomers. Flow channelizer 32 includes opposed proximal and distal ends 36 and 38. A generally cylindrical outer surface extends between proximal and distal ends 36 and 38, and defines a major diameter "b", which is slightly greater than the inside diameter "a" of chamber 20 in syringe barrel 12. Thus, flow channelizer 32 can be resiliently and frictionally retained within chamber 20. The outer cylindrical surface of flow channelizer 32 is further characterized by at least one and preferably a plurality of flutes 40. The flutes are sufficiently deep to define axially extending channels adjacent cylindrical chamber wall 18 of syringe barrel 12. As will be explained further herein, helically extending flutes 40 are preferred because helically extending flutes create a vortex of flowing diluent or a swirling action of diluent to achieve efficient mixing of lyophilized medication.

Proximal end 36 of flow channelizer 32 includes an aperture 42 extending axially therein. Aperture 42 is of generally cylindrical shape, and defines a major diameter "c". Preferably, a plurality of ribs 44 extend axially along aperture 42 and define a minor diameter "d".

Stopper 34 can be made of resilient material such as natural rubber, synthetic rubber or thermoplastic elastomers and also is of generally cylindrical configuration. More particularly, stopper 34 includes opposed proximal and distal ends 46 and 48. External portions of stopper 34 between proximal and distal ends 46 and 48 define a plurality of annular ribs 50 with an outside diameter "e" which is slightly greater than inside diameter "a" of chamber 20 in syringe barrel 12. Thus, annular ribs 50 resiliently engage interior portions of cylindrical chamber wall 18 in sliding fluid-tight engagement. As will be explained further herein, stopper 34 enables efficient stoppering of syringe barrel 12 and also contributes to the flowing of diluent into chamber 20 and the ejection of reconstituted liquid medication therefrom.

Distal end 48 of stopper 34 includes an axial extending mating projection 52 of generally cylindrical configuration.

Mating projection 52 defines an outside diameter "f" which is slightly greater than the minor diameter "d" defined by ribs 44 in mounting cavity 42 of flow channelizer 32. Thus, projection 52 can be releasably engaged in mounting aperture 42 at proximal end 36 of flow channelizer 32. The configuration described herein is merely representative of many possible configurations which can be used to make the stopper and the flow channelizer releasably engageable. The projection could be placed on the proximal end of the flow channelizer and the recess on the distal end of the stopper. Multiple projections and recesses can be used as well as various latching structures.

Proximal end 46 of stopper 34 defines an axially extending rod mounting aperture 54. The rod mounting aperture includes an array of internal threads for threaded engagement with a plunger rod, as explained further herein. A plunger rod 56 includes a threaded distal end 58 which is threadedly engageable in threaded aperture 54 at proximal end 46 of stopper 34. It is within the purview of this invention to include other structures for joining the distal end of the plunger rod and the proximal end of the stopper such as snap-fit arrangement or a bayonet-type fitting. The stopper can also include a rigid insert to accept the plunger rod.

The syringe assembly 10 further includes a needle assembly 60. Needle assembly 60 includes an elongate needle cannula 62 having a proximal end 64, a distal end 66 and a lumen 68 extending therebetween. Proximal end 64 of needle cannula 62 is securely and substantially permanently mounted to a mounting hub 70 which is configured for threaded engagement with luer collar 26 and distal end 16 of syringe barrel 12.

Syringe assembly 10 is used by sealingly engaging tip cap 28 over tip 22 of syringe barrel 12, and supporting syringe barrel 12 so that proximal end 14 is gravitationally upward as shown in FIG. 7. A selected dose of liquid medication 72 then is deposited in chamber 20 of syringe barrel 12. Flow channelizer 32 of plunger assembly 30 is then inserted into open proximal end 14 of syringe barrel 12. Thus, flutes 40 in flow channelizer 32 enable communication between chamber 20 of syringe barrel 12 and ambient atmosphere surrounding syringe barrel 12. The filled and stoppered syringe barrel is then presented to a lyophilizing apparatus for freeze drying medication 72. The lyophilizing process converts liquid portions of medication 72 into a vapor which is drawn from chamber 20 through times 40 so that dry medication 73 remains in the chamber.

Figure 11:
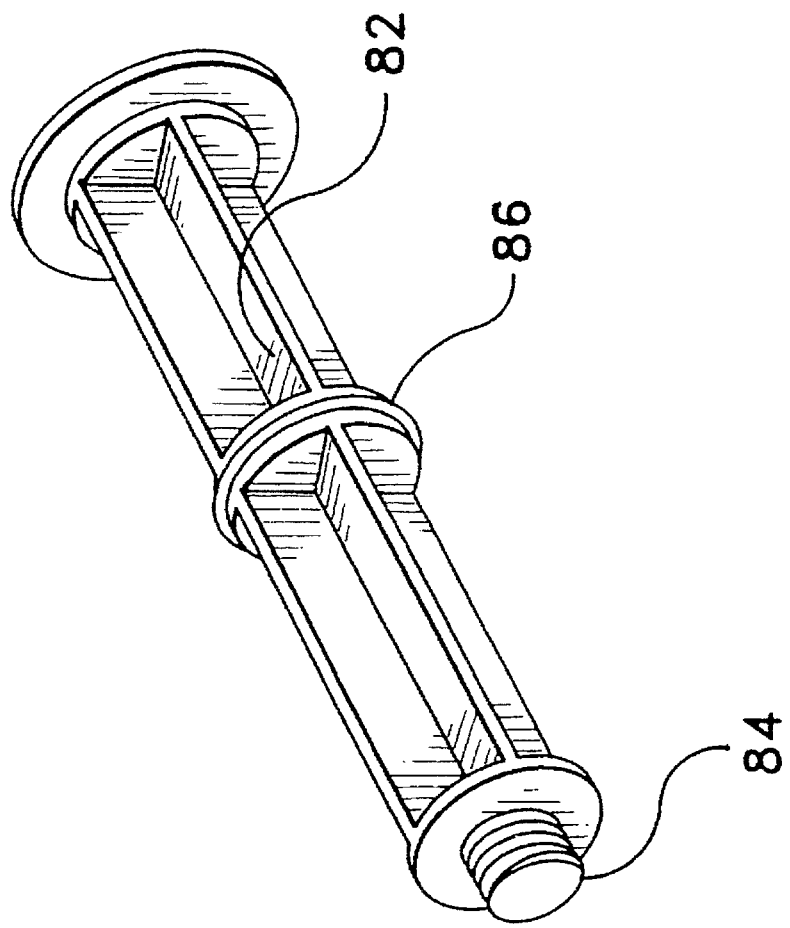
FIG. 11 is an alternate plunger rod construction for use in the syringe assembly.

A vacuum is next applied to the lyophilizing apparatus to provide at least a partial vacuum both within chamber 20 and in regions of the lyophilizing apparatus external of syringe barrel 12. Next, as shown in FIG. 8, a shelf 74 of the lyophilizing apparatus is lowered into contact with proximal end 46 of stopper 34 to urge ribs 50 into sealing engagement with cylindrical chamber wall 18 of syringe barrel 12. The lyophilizing apparatus then is operated to restore atmospheric pressure. However, this increase in pressure will affect only portions of the lyophilizing apparatus external chamber 20. The pressure differential on opposed sides of plunger assembly 30 will cause the entire plunger assembly to slide distally in syringe barrel 12 and toward the lyophilized medication 73 as shown in FIG. 9. This distal movement of plunger assembly 30 will terminate when the pressure between the chamber containing the lyophilized medication 73 and plunger assembly 30 approximately equals the atmospheric pressure external of syringe barrel 12. After the process is complete the open proximal end of the barrel may be sealed to prevent contamination of the walls of chamber 20. The sealing can be accomplished with a rubber or plastic plug such as plug 79 which has a boss 80 having a diameter slightly larger than the inside diameter of the chamber. Sealing may also be accomplished by additional structure on the plunger rod such as second stopper like section on the plunger rod spaced proximally from stopper 34. Such a plunger rod is illustrated in FIG. 11. Plunger rod 82 includes threaded distal end 84 and a central groove holding "O" ring 86 which seals the chamber inside diameter while the filled syringe is in storage.

The syringe barrel with the lyophilized medication 73 sealed therein by tip cap 28 and plunger assembly 30 then can be packaged and shipped for subsequent reconstitution and use. Reconstitution is achieved with a diluent 75 as shown in FIG. 10. More particularly, diluent 75 is stored in a container 76, such as a vial or ampule. Diluent 75 is accessed by initially threadedly engaging the distal end of plunger rod 56 into the threaded aperture in proximal end 46 of stopper 34. Tip cap 28 then is removed from tip 22 of syringe barrel 12, and hub 70 of needle cannula assembly 60 is threadedly engaged with luer collar 26 of syringe barrel 12. Thus, lumen 68 through needle cannula 62 is placed in communication with passage 24 through tip 22 and with lyophilized medication 73 in chamber 20.

Reconstitution is achieved as shown in FIG. 10 by placing distal end 66 of needle cannula 62 in diluent 75. Plunger rod 56 then is moved proximally to draw diluent 75 into chamber 20 for mixture with previously lyophilized medication 73. The proximal movement of plunger rod 56 causes stopper 34 to move proximally. However, frictional forces between flow channelizer 32 and cylindrical chamber wall 18 of syringe barrel 12 exceeds the retention forces between stopper 34 and flow channelizer 32. Thus, flow channelizer 32 will remain resiliently and frictionally engaged with cylindrical wall 18 of syringe barrel 12, while stopper 34 will move proximally in syringe barrel 12 due to the direct mechanical engagement between stopper 34 and plunger rod 56. This separation of flow channelizer 32 from stopper 34 creates a mixing chamber 78 between the separated flow channelizer 32 and stopper 34. The low pressure created within the mixing chamber 78 causes diluent 75 to be drawn through needle cannula 62, and through portions of chamber 20 disposed distally of flow channelizer 32. Diluent 75 will continue through the channels defined by flutes 40 and into mixing chamber 78. The helical configuration of flutes 40 creates a vortex or swirling action that enhances mixing of diluent 75 and the lyophilized medication 73 in the mixing chamber 78. Syringe assembly 10 then can be used substantially in the standard manner by urging plunger rod 56 in a distal direction. If necessary, the needle assembly 60 used for reconstitution of the lyophilized medication can be removed and replaced with a needle cannula more suitable for injection into a patient. Also, it is possible to reconstitute the medication by connecting the barrel tip directly to a liquid reservoir without the use of a needle.

The syringe assembly of the instant invention can also be used with dry medication which has not been produced by a lyophilization process such as other dry medication in powder, granular or solid configurations.

While the invention has been described with respect to a preferred embodiment, it is apparent that various changes can be made without departing from the scope of the invention as defined by the appended claims.

What is claimed is:

1. A plunger assembly for a cylindrical syringe barrel to enable lyophilization of an injectable medication, reconstitution of the lyophilized medication and injection thereof, said plunger assembly comprising:

a generally cylindrical flow channelizer having opposed proximal and distal ends and a generally cylindrical outer surface extending therebetween, at least one fluid flow channel extending between said proximal and distal ends of said flow channelizer;

a stopper having opposed proximal and distal ends, said proximal end of said stopper including mounting means for engaging a plunger rod, portions of said stopper intermediate said proximal and distal ends being configured for sliding fluid-tight engagement with said syringe barrel; and engagement means for releasably engaging said proximal end of said flow channelizer and said distal end of said stopper, wherein said distal end of said stopper is releasable from the proximal end of the flow channelizer to define a reconstitution chamber therebetween for said lyophilized medication in fluid communication with said at least one fluid flow channel.

2. The plunger assembly of claim 1, wherein said at least one fluid flow channel includes a plurality of fluid flow channels.

3. The plunger assembly of claim 2 wherein said fluid flow channels of said flow channelizer comprise a plurality of flutes extending helically around said flow channelizer.

4. The plunger assembly of claim 1, wherein said engagement means comprises complementary structures at said proximal end of said flow channelizer and said distal end of said stopper.

5. The plunger assembly of claim 4, wherein said engagement means comprises at least one aperture extending distally into said proximal end of said flow channelizer and at least one projection extending from the distal end of said stopper and said projection being dimensioned for releasable engagement in said aperture of said flow channelizer.

6. The plunger assembly of claim 1, wherein said mounting means of said stopper comprises a threaded aperture extending into said proximal end of said stopper.

7. The plunger assembly of claim 1, wherein said stopper comprises a plurality of annular ribs dimensioned for sliding fluid-tight engagement with said syringe barrel.

8. A syringe assembly comprising:

a syringe barrel having an open proximal end, a distal end and a substantially cylindrical chamber wall extending therebetween to define a fluid receiving chamber, a passage extending through said distal end and communicating with said chamber;

a stopper dimensioned and disposed for sliding fluid-tight engagement in said chamber of said syringe barrel, said stopper having opposed proximal and distal ends;

means for releasably sealing said passage to isolate said chamber from the environment;

an elongate plunger rod having a proximal end and a distal end engaging said proximal end of said stopper; and a flow channelizer slidably disposed in said chamber of said syringe barrel between said stopper and said distal end of said syringe barrel, said flow channelizer having opposed proximal and distal ends and at least one fluid flow channel extending therebetween, whereby distally directed forces on said plunger rod urge said stopper and said flow channelizer in a distal direction in said syringe barrel, whereby proximally directed forces on said plunger rod cause said stopper to move proximally and away from said flow channelizer to define a mixing chamber therebetween in fluid communication with said at least one fluid flow channel.

9. The syringe assembly of claim 8, further including engagement means for releasably engaging said stopper and said flow channelizer.

10. The syringe assembly of claim 9 wherein said engagement means comprises complementary structures at said distal end of said stopper and said proximal end of said flow channelizer.

11. The syringe assembly of claim 9, wherein said engagement means comprises at least one aperture in the proximal end of said channelizer and at least one projection in said distal end of said stopper, said aperture and said projection being dimensioned for releasable engagement with one another.

12. The syringe assembly of claim 8 wherein said at least one fluid flow channel includes a plurality of fluid flow channels.

13. The syringe assembly of claim 12, wherein said fluid flow channels of said flow channelizer are helically oriented around said flow channelizer from said distal end thereof to said proximal end.

14. The syringe assembly of claim 8, wherein said stopper includes a threaded aperture in said proximal end of said stopper, said plunger rod including a threaded distal end for engagement with said threaded aperture of said stopper.

15. The syringe assembly of claim 8 further including sealing means on said plunger rod positioned proximally from said distal end of said plunger rod and said stopper for sealing said chamber from contamination.

16. The syringe assembly of claim 15 wherein said sealing means includes a resilient O-ring positioned around said plunger rod.

17. The syringe assembly of claim 8 further including medication in said chamber.

18. The syringe assembly of claim 17 herein said medication is selected from the group consisting of: lyophilized medication, powdered medication, and granular medication.

19. The syringe assembly of claim 8 wherein said flow channelizer is made of material selected from the group consisting of natural rubber, synthetic rubber and thermoplastic elastomers.

20. The syringe assembly of claim 8 wherein said barrel is made from material selected from the group consisting of glass and plastic.

21. A process for lyophilizing an injectable medication, said process comprising the steps of:

providing a syringe barrel with an open proximal end, a distal end and a cylindrical chamber wall extending therebetween and defining a fluid receiving chamber, a tip projecting from said distal end of said syringe and having a passage extending therethrough and communicating with said chamber;

sealing said passage in said tip;

placing a liquid medication in said chamber;

providing a plunger assembly having a distally disposed flow channelizer with opposed proximal and distal ends and at least one fluid flow channel extending therebetween and a stopper dimensioned for sliding fluid-tight engagement with said cylindrical chamber wall and disposed adjacent said flow channelizer and proximally thereof;

inserting said flow channelizer of said plunger assembly into said proximal end of said syringe barrel;

lyophilizing said liquid medication in said chamber; and urging said plunger assembly distally into said syringe barrel such that said stopper thereof seals said lyophilized medication in said chamber.

22. The process of claim 21 further including the additional steps for reconstituting said medication comprising:

unsealing said passage in said tip;

placing said passage in said tip in communication with a diluent; and urging said stopper proximally and away from said flow channelizer for urging said diluent through said passage in said tip and through said fluid flow channels for reconstituting said lyophilized medication.

23. The process of claim 22, further comprising the steps of providing a plunger rod, engaging said plunger rod with said stopper and urging said plunger rod in a proximal direction to separate said stopper from said flow channelizer.

24. The process of claim 21, further comprising the step of creating a vacuum in said chamber after lyophilizing said medication and prior to urging said stopper into sliding fluid-tight engagement with said cylindrical wall of said chamber.

* * * * *